US009492637B2

(12) United States Patent
Garrison et al.

(10) Patent No.: US 9,492,637 B2
(45) Date of Patent: Nov. 15, 2016

(54) TRANSCAROTID NEUROVASCULAR CATHETER

(71) Applicant: Silk Road Medical, Inc., Sunnyvale, CA (US)

(72) Inventors: Michi E. Garrison, Sunnyvale, CA (US); Scott D. Wilson, Sunnyvale, CA (US)

(73) Assignee: Silk Road Medical, Inc., Sunnyvale, CA (US)

(*) Notice: Subject to any disclaimer, the term of this patent is extended or adjusted under 35 U.S.C. 154(b) by 0 days.

(21) Appl. No.: 15/050,039

(22) Filed: Feb. 22, 2016

(65) Prior Publication Data

US 2016/0166804 A1    Jun. 16, 2016

Related U.S. Application Data

(63) Continuation of application No. 14/569,365, filed on Dec. 12, 2014, now Pat. No. 9,265,512.

(60) Provisional application No. 62/083,128, filed on Nov. 21, 2014, provisional application No. 62/075,169, (Continued)

(51) Int. Cl.
    *A61M 25/00* (2006.01)
    *A61M 25/01* (2006.01)

(52) U.S. Cl.
    CPC .......... *A61M 25/01* (2013.01); *A61M 25/0023* (2013.01); *A61M 25/0043* (2013.01)

(58) Field of Classification Search
    CPC ........... A61M 25/01; A61M 25/0041; A61M 25/0053; A61M 25/0054; A61M 25/0063; A61M 25/0068

USPC .......................................... 604/523, 525, 534
See application file for complete search history.

(56) References Cited

U.S. PATENT DOCUMENTS

| 4,771,777 | A | 9/1988 | Horzewski et al. |
| 4,840,690 | A | 6/1989 | Melinyshyn et al. |
| 4,865,581 | A | 9/1989 | Lundquist et al. |
| 4,921,478 | A | 5/1990 | Solano et al. |
| 4,921,479 | A | 5/1990 | Grayzel |

(Continued)

FOREIGN PATENT DOCUMENTS

| DE | 102006039236 A1 | 2/2008 |
| EP | 0427429 A2 | 5/1991 |
| EP | 1440663 A1 | 7/2004 |
| JP | 2003-522560 A | 7/2003 |

(Continued)

OTHER PUBLICATIONS

Adami, M.D., et al., (2002) "Use of the Parodi Anti-Embolism System in Carotid Stenting: Italian Trial Results" J Endovasc Ther 9:147-154.

(Continued)

*Primary Examiner* — Gerald Landry, II
(74) *Attorney, Agent, or Firm* — Fred C. Hernandez; Mintz Levin Cohn Ferris Glovsky and Popeo, P.C.

(57) ABSTRACT

An interventional catheter for treating an artery includes an elongated body sized and shaped to be transcervically introduced into a common carotid artery at an access location in the neck. The elongated body has an overall length such that the distal most section can be positioned in an intracranial artery and at least a portion of the proximal most section is positioned in the common carotid artery during use.

19 Claims, 6 Drawing Sheets

Related U.S. Application Data filed on Nov. 4, 2014, provisional application No. 62/075,101, filed on Nov. 4, 2014, provisional application No. 62/046,112, filed on Sep. 4, 2014, provisional application No. 62/029,799, filed on Jul. 28, 2014, provisional application No. 61/919,945, filed on Dec. 23, 2013.

(56) References Cited

U.S. PATENT DOCUMENTS

| | | |
|---|---|---|
| 4,946,440 A | 8/1990 | Hall |
| 5,135,484 A | 8/1992 | Wright |
| 5,250,060 A | 10/1993 | Carbo et al. |
| 5,312,356 A | 5/1994 | Engelson et al. |
| RE34,633 E | 6/1994 | Sos et al. |
| 5,324,262 A | 6/1994 | Fischell et al. |
| 5,328,471 A | 7/1994 | Slepian |
| 5,380,284 A | 1/1995 | Don Michael |
| 5,429,605 A | 7/1995 | Richling et al. |
| 5,437,632 A | 8/1995 | Engelson |
| 5,443,454 A | 8/1995 | Tanabe et al. |
| 5,454,795 A | 10/1995 | Samson |
| 5,476,450 A | 12/1995 | Ruggio |
| 5,484,412 A | 1/1996 | Pierpont |
| 5,484,418 A | 1/1996 | Quiachon et al. |
| 5,492,530 A | 2/1996 | Fischell et al. |
| 5,496,294 A | 3/1996 | Hergenrother et al. |
| 5,522,836 A | 6/1996 | Palermo |
| 5,542,937 A | 8/1996 | Chee et al. |
| 5,558,635 A | 9/1996 | Cannon |
| 5,573,520 A | 11/1996 | Schwartz et al. |
| 5,599,326 A | 2/1997 | Carter |
| 5,628,754 A | 5/1997 | Shevlin et al. |
| 5,658,264 A | 8/1997 | Samson |
| 5,667,499 A | 9/1997 | Welch et al. |
| 5,695,483 A | 12/1997 | Samson |
| 5,702,373 A | 12/1997 | Samson |
| 5,707,376 A | 1/1998 | Kavteladze et al. |
| 5,730,734 A | 3/1998 | Adams et al. |
| 5,749,849 A | 5/1998 | Engelson |
| 5,749,858 A | 5/1998 | Cramer |
| 5,794,629 A | 8/1998 | Frazee |
| 5,795,341 A | 8/1998 | Samson |
| 5,810,869 A | 9/1998 | Kaplan et al. |
| 5,827,229 A | 10/1998 | Auth et al. |
| 5,833,650 A | 11/1998 | Imran |
| 5,836,926 A | 11/1998 | Peterson et al. |
| 5,846,251 A | 12/1998 | Hart |
| 5,851,210 A | 12/1998 | Torossian |
| 5,853,400 A | 12/1998 | Samson |
| 5,876,367 A | 3/1999 | Kaganov et al. |
| 5,876,386 A | 3/1999 | Samson |
| 5,882,334 A | 3/1999 | Sepetka et al. |
| 5,895,399 A | 4/1999 | Barbut et al. |
| 5,908,407 A | 6/1999 | Frazee et al. |
| 5,913,848 A | 6/1999 | Luther et al. |
| 5,916,208 A | 6/1999 | Luther et al. |
| 5,921,952 A | 7/1999 | Desmond, III et al. |
| 5,928,192 A | 7/1999 | Maahs |
| 5,935,122 A | 8/1999 | Fourkas et al. |
| 5,938,645 A | 8/1999 | Gordon |
| 5,957,882 A | 9/1999 | Nita et al. |
| 5,976,093 A | 11/1999 | Jang |
| 5,976,178 A | 11/1999 | Goldsteen et al. |
| 5,997,508 A | 12/1999 | Lunn et al. |
| 6,004,310 A | 12/1999 | Bardsley et al. |
| 6,013,085 A | 1/2000 | Howard |
| 6,022,340 A | 2/2000 | Sepetka et al. |
| 6,030,369 A | 2/2000 | Engelson et al. |
| 6,033,388 A | 3/2000 | Nordstrom et al. |
| 6,044,845 A | 4/2000 | Lewis |
| 6,053,903 A | 4/2000 | Samson |
| 6,053,904 A | 4/2000 | Scribner et al. |
| 6,071,263 A | 6/2000 | Kirkman |
| 6,074,357 A | 6/2000 | Kaganov et al. |
| 6,074,398 A | 6/2000 | Leschinsky |
| 6,090,072 A | 7/2000 | Kratoska et al. |
| 6,110,139 A | 8/2000 | Loubser |
| 6,139,524 A | 10/2000 | Killion |
| 6,146,370 A | 11/2000 | Barbut |
| 6,146,373 A | 11/2000 | Cragg et al. |
| 6,146,415 A | 11/2000 | Fitz |
| 6,152,909 A | 11/2000 | Bagaoisan et al. |
| 6,152,912 A | 11/2000 | Jansen et al. |
| 6,159,230 A | 12/2000 | Samuels |
| 6,161,547 A | 12/2000 | Barbut |
| 6,165,199 A | 12/2000 | Barbut |
| 6,176,844 B1 | 1/2001 | Lee |
| 6,197,016 B1 | 3/2001 | Fourkas et al. |
| 6,206,868 B1 | 3/2001 | Parodi |
| 6,210,370 B1 | 4/2001 | Chi-Sing et al. |
| 6,234,971 B1 | 5/2001 | Jang |
| 6,254,628 B1 | 7/2001 | Wallace et al. |
| 6,258,080 B1 | 7/2001 | Samson |
| 6,270,477 B1 | 8/2001 | Bagaoisan et al. |
| 6,277,139 B1 | 8/2001 | Levinson et al. |
| 6,287,319 B1 | 9/2001 | Aboul-Hosn et al. |
| 6,295,989 B1 | 10/2001 | Connors, III |
| 6,295,990 B1 | 10/2001 | Lewis et al. |
| 6,306,106 B1 | 10/2001 | Boyle |
| 6,306,163 B1 | 10/2001 | Fitz |
| 6,364,900 B1 | 4/2002 | Heuser |
| 6,368,316 B1 | 4/2002 | Jansen et al. |
| 6,368,344 B1 | 4/2002 | Fitz |
| 6,379,325 B1 | 4/2002 | Benett et al. |
| 6,383,172 B1 | 5/2002 | Barbut |
| 6,413,235 B1 | 7/2002 | Parodi |
| 6,423,032 B2 | 7/2002 | Parodi |
| 6,423,086 B1 | 7/2002 | Barbut et al. |
| 6,428,531 B1 | 8/2002 | Visuri et al. |
| 6,435,189 B1 | 8/2002 | Lewis et al. |
| 6,436,087 B1 | 8/2002 | Lewis et al. |
| 6,454,741 B1 | 9/2002 | Muni et al. |
| 6,458,151 B1 | 10/2002 | Saltiel |
| 6,464,664 B1 | 10/2002 | Jonkman et al. |
| 6,481,439 B1 | 11/2002 | Lewis et al. |
| 6,482,172 B1 | 11/2002 | Thramann |
| 6,482,217 B1 | 11/2002 | Pintor et al. |
| 6,508,824 B1 | 1/2003 | Flaherty et al. |
| 6,517,520 B2 | 2/2003 | Chang et al. |
| 6,527,746 B1 | 3/2003 | Oslund et al. |
| 6,533,800 B1 | 3/2003 | Barbut |
| 6,540,712 B1 | 4/2003 | Parodi et al. |
| 6,544,276 B1 | 4/2003 | Azizi |
| 6,549,800 B1 * | 4/2003 | Atalar ............ A61B 5/418 |
| | | 324/244 |
| 6,551,268 B1 | 4/2003 | Kaganov et al. |
| 6,555,057 B1 | 4/2003 | Barbut et al. |
| 6,562,049 B1 | 5/2003 | Norlander et al. |
| 6,562,052 B2 | 5/2003 | Nobles et al. |
| 6,582,390 B1 | 6/2003 | Sanderson |
| 6,582,396 B1 | 6/2003 | Parodi |
| 6,582,448 B1 | 6/2003 | Boyle et al. |
| 6,595,953 B1 | 7/2003 | Coppi et al. |
| 6,595,980 B1 | 7/2003 | Barbut |
| 6,605,074 B2 | 8/2003 | Zadno-Azizi et al. |
| 6,612,999 B2 | 9/2003 | Brennan et al. |
| 6,623,471 B1 | 9/2003 | Barbut |
| 6,623,491 B2 | 9/2003 | Thompson |
| 6,623,518 B2 | 9/2003 | Thompson et al. |
| 6,626,886 B1 | 9/2003 | Barbut |
| 6,632,236 B2 | 10/2003 | Hogendijk |
| 6,635,070 B2 | 10/2003 | Leeflang et al. |
| 6,638,243 B2 | 10/2003 | Kupiecki |
| 6,638,245 B2 | 10/2003 | Miller et al. |
| 6,641,573 B1 | 11/2003 | Parodi |
| 6,645,160 B1 | 11/2003 | Heesch |
| 6,645,222 B1 | 11/2003 | Parodi et al. |
| 6,652,480 B1 | 11/2003 | Imran et al. |
| 6,656,152 B2 | 12/2003 | Putz |
| 6,663,650 B2 | 12/2003 | Sepetka et al. |
| 6,663,652 B2 | 12/2003 | Daniel et al. |
| 6,679,893 B1 | 1/2004 | Tran |
| 6,682,505 B2 | 1/2004 | Bates et al. |

(56) References Cited

U.S. PATENT DOCUMENTS

| | | |
|---|---|---|
| 6,685,722 B1 | 2/2004 | Rosenbluth et al. |
| 6,702,782 B2 | 3/2004 | Miller et al. |
| 6,711,436 B1 | 3/2004 | Duhaylongsod |
| 6,719,717 B1 | 4/2004 | Johnson et al. |
| 6,730,104 B1 | 5/2004 | Sepetka et al. |
| 6,733,517 B1 | 5/2004 | Collins |
| 6,749,627 B2 | 6/2004 | Thompson et al. |
| 6,755,847 B2 | 6/2004 | Eskuri |
| 6,758,854 B1 | 7/2004 | Butler et al. |
| 6,764,464 B2 | 7/2004 | McGuckin, Jr. et al. |
| 6,790,204 B2 | 9/2004 | Zadno-Azizi et al. |
| 6,824,545 B2 | 11/2004 | Sepetka et al. |
| 6,827,730 B1 | 12/2004 | Leschinsky |
| 6,837,881 B1 | 1/2005 | Barbut |
| 6,840,949 B2 | 1/2005 | Barbut |
| 6,849,068 B1 | 2/2005 | Bagaoisan et al. |
| 6,855,136 B2 | 2/2005 | Dorros et al. |
| 6,884,235 B2 | 4/2005 | McGuckin, Jr. et al. |
| 6,902,540 B2 | 6/2005 | Dorros et al. |
| 6,905,490 B2 | 6/2005 | Parodi |
| 6,905,505 B2 | 6/2005 | Nash et al. |
| 6,908,474 B2 | 6/2005 | Hogendijk et al. |
| 6,929,632 B2 | 8/2005 | Nita et al. |
| 6,929,634 B2 | 8/2005 | Dorros et al. |
| 6,936,060 B2 | 8/2005 | Hogendijk et al. |
| 6,958,059 B2 | 10/2005 | Zadno-Azizi |
| 6,960,189 B2 | 11/2005 | Bates et al. |
| 6,972,030 B2 | 12/2005 | Lee et al. |
| 7,001,400 B1 | 2/2006 | Modesitt et al. |
| 7,004,924 B1 | 2/2006 | Brugger et al. |
| 7,004,931 B2 | 2/2006 | Hogendijk |
| 7,004,952 B2 | 2/2006 | Nobles et al. |
| 7,022,100 B1 | 4/2006 | Aboul-Hosn et al. |
| 7,029,488 B2 | 4/2006 | Schonholz et al. |
| 7,033,336 B2 | 4/2006 | Hogendijk |
| 7,033,344 B2 | 4/2006 | Imran |
| 7,048,758 B2 | 5/2006 | Boyle et al. |
| 7,063,714 B2 | 6/2006 | Dorros et al. |
| 7,083,594 B2 | 8/2006 | Coppi |
| 7,104,979 B2 | 9/2006 | Jansen et al. |
| 7,108,677 B2 | 9/2006 | Courtney et al. |
| 7,144,386 B2 | 12/2006 | Korkor et al. |
| 7,150,712 B2 | 12/2006 | Buehlmann et al. |
| 7,152,605 B2 | 12/2006 | Khairkhahan et al. |
| 7,166,088 B2 | 1/2007 | Heuser |
| 7,169,165 B2 | 1/2007 | Belef et al. |
| 7,172,621 B2 | 2/2007 | Theron |
| 7,223,253 B2 | 5/2007 | Hogendijk |
| 7,232,452 B2 | 6/2007 | Adams et al. |
| 7,250,042 B2 | 7/2007 | Kataishi et al. |
| 7,306,585 B2 | 12/2007 | Ross |
| 7,309,334 B2 | 12/2007 | von Hoffmann |
| 7,367,982 B2 | 5/2008 | Nash et al. |
| 7,374,560 B2 | 5/2008 | Ressemann et al. |
| 7,374,561 B2 | 5/2008 | Barbut |
| 7,384,412 B2 | 6/2008 | Coppi |
| 7,402,151 B2 | 7/2008 | Rosenman et al. |
| 7,422,579 B2 | 9/2008 | Wahr et al. |
| 7,458,980 B2 | 12/2008 | Barbut |
| 7,497,844 B2 | 3/2009 | Spear et al. |
| 7,524,303 B1 | 4/2009 | Don Michael et al. |
| 7,534,250 B2 | 5/2009 | Schaeffer et al. |
| 7,731,683 B2 | 6/2010 | Jang et al. |
| 7,766,049 B2 | 8/2010 | Miller et al. |
| 7,766,820 B2 | 8/2010 | Core |
| 7,806,906 B2 | 10/2010 | Don Michael |
| 7,815,626 B1 | 10/2010 | McFadden et al. |
| 7,842,065 B2 | 11/2010 | Belef et al. |
| 7,867,216 B2 | 1/2011 | Wahr et al. |
| 7,905,856 B2 | 3/2011 | McGuckin, Jr. et al. |
| 7,905,877 B1 | 3/2011 | Jimenez et al. |
| 7,909,812 B2 | 3/2011 | Jansen et al. |
| 7,927,309 B2 | 4/2011 | Palm |
| 7,927,347 B2 | 4/2011 | Hogendijk et al. |
| 7,972,308 B2 | 7/2011 | Putz |
| 7,998,104 B2 | 8/2011 | Chang |
| 8,029,533 B2 | 10/2011 | Bagaoisan et al. |
| 8,052,640 B2 | 11/2011 | Fiorella et al. |
| 8,066,757 B2 | 11/2011 | Ferrera et al. |
| 8,142,413 B2 | 3/2012 | Root et al. |
| RE43,300 E | 4/2012 | Saadat et al. |
| 8,152,782 B2 | 4/2012 | Jang et al. |
| 8,157,760 B2 | 4/2012 | Criado et al. |
| 8,181,324 B2 | 5/2012 | McFadden et al. |
| 8,221,348 B2 | 7/2012 | Hackett et al. |
| 8,231,600 B2 | 7/2012 | von Hoffmann |
| 8,252,010 B1 | 8/2012 | Raju et al. |
| 8,292,850 B2 | 10/2012 | Root et al. |
| 8,343,089 B2 | 1/2013 | Chang |
| 8,414,516 B2 | 4/2013 | Chang |
| 8,545,552 B2 | 10/2013 | Garrison et al. |
| 8,574,245 B2 | 11/2013 | Garrison et al. |
| 8,870,805 B2 | 10/2014 | Chang |
| 8,961,549 B2 | 2/2015 | Conn |
| 9,126,018 B1 | 9/2015 | Garrison |
| 2001/0044598 A1 | 11/2001 | Parodi |
| 2001/0049486 A1 | 12/2001 | Evans et al. |
| 2001/0049517 A1 | 12/2001 | Zadno-Azizi et al. |
| 2002/0087119 A1 | 7/2002 | Parodi |
| 2002/0128679 A1 | 9/2002 | Turovskiy et al. |
| 2002/0133111 A1 | 9/2002 | Shadduck |
| 2002/0151922 A1 | 10/2002 | Hogendijk et al. |
| 2002/0156455 A1 | 10/2002 | Barbut |
| 2002/0156460 A1* | 10/2002 | Ye .................. A61L 29/085 604/534 |
| 2002/0165598 A1 | 11/2002 | Wahr et al. |
| 2002/0173815 A1 | 11/2002 | Hogendijk et al. |
| 2002/0183783 A1 | 12/2002 | Shadduck |
| 2003/0040762 A1 | 2/2003 | Dorros et al. |
| 2003/0065356 A1 | 4/2003 | Tsugita et al. |
| 2003/0069468 A1 | 4/2003 | Bolling et al. |
| 2003/0078562 A1 | 4/2003 | Makower et al. |
| 2003/0186203 A1 | 10/2003 | Aboud |
| 2003/0212304 A1 | 11/2003 | Lattouf |
| 2003/0212384 A1 | 11/2003 | Hayden |
| 2004/0059243 A1 | 3/2004 | Flores et al. |
| 2004/0116878 A1 | 6/2004 | Byrd et al. |
| 2004/0133232 A1 | 7/2004 | Rosenbluth et al. |
| 2004/0138608 A1 | 7/2004 | Barbut et al. |
| 2004/0210194 A1 | 10/2004 | Bonnette et al. |
| 2005/0090802 A1* | 4/2005 | Connors .......... A61M 25/0017 604/500 |
| 2005/0131453 A1 | 6/2005 | Parodi |
| 2005/0154344 A1 | 7/2005 | Chang |
| 2005/0154349 A1 | 7/2005 | Renz et al. |
| 2005/0209559 A1 | 9/2005 | Thornton et al. |
| 2005/0273051 A1 | 12/2005 | Coppi |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0089618 A1* | 4/2006 | McFerran ......... A61M 25/0041 604/525 |
| 2006/0135961 A1* | 6/2006 | Rosenman ........ A61M 25/0045 606/108 |
| 2006/0200191 A1 | 9/2006 | Zadno-Azizi |
| 2006/0271098 A1 | 11/2006 | Peacock |
| 2007/0021778 A1 | 1/2007 | Carly |
| 2007/0073264 A1* | 3/2007 | Stedman ............ A61K 48/0075 604/500 |
| 2007/0173784 A1 | 7/2007 | Johansson et al. |
| 2007/0197956 A1 | 8/2007 | Le et al. |
| 2007/0198028 A1 | 8/2007 | Miloslavski et al. |
| 2007/0198049 A1 | 8/2007 | Barbut |
| 2008/0082107 A1 | 4/2008 | Miller et al. |
| 2008/0140010 A1 | 6/2008 | Kennedy et al. |
| 2008/0177245 A1 | 7/2008 | Mesallum |
| 2008/0200946 A1 | 8/2008 | Braun et al. |
| 2009/0018455 A1 | 1/2009 | Chang |
| 2009/0024072 A1 | 1/2009 | Criado et al. |
| 2009/0030400 A1 | 1/2009 | Bose et al. |
| 2009/0198172 A1 | 8/2009 | Garrison et al. |
| 2009/0254166 A1 | 10/2009 | Chou et al. |
| 2009/0299393 A1 | 12/2009 | Martin et al. |
| 2010/0004607 A1 | 1/2010 | Wilson et al. |

(56) References Cited

U.S. PATENT DOCUMENTS

| | | | |
|---|---|---|---|
| 2010/0042118 A1 | 2/2010 | Garrison et al. | |
| 2010/0063479 A1 | 3/2010 | Merdan et al. | |
| 2010/0063480 A1* | 3/2010 | Shireman | A61M 25/0054 604/528 |
| 2010/0094330 A1 | 4/2010 | Barbut | |
| 2010/0114017 A1 | 5/2010 | Lenker et al. | |
| 2010/0145308 A1* | 6/2010 | Layman | A61B 1/00071 604/523 |
| 2010/0185216 A1 | 7/2010 | Garrison et al. | |
| 2010/0204672 A1 | 8/2010 | Lockhart et al. | |
| 2010/0204684 A1 | 8/2010 | Garrison et al. | |
| 2010/0217276 A1 | 8/2010 | Garrison et al. | |
| 2010/0228269 A1 | 9/2010 | Garrison et al. | |
| 2010/0256600 A1 | 10/2010 | Ferrera | |
| 2010/0318097 A1 | 12/2010 | Ferrera et al. | |
| 2011/0009875 A1 | 1/2011 | Grandfield et al. | |
| 2011/0034986 A1 | 2/2011 | Chou et al. | |
| 2011/0087147 A1 | 4/2011 | Garrison et al. | |
| 2011/0112567 A1 | 5/2011 | Lenker et al. | |
| 2011/0125181 A1 | 5/2011 | Brady et al. | |
| 2011/0152760 A1 | 6/2011 | Parker | |
| 2011/0238041 A1* | 9/2011 | Lim | A61M 25/0045 604/527 |
| 2012/0109044 A1* | 5/2012 | Santamore | A61B 17/00234 604/22 |
| 2012/0310212 A1 | 12/2012 | Fischell et al. | |
| 2013/0035628 A1 | 2/2013 | Garrison et al. | |
| 2013/0184735 A1 | 7/2013 | Fischell et al. | |
| 2013/0197621 A1 | 8/2013 | Ryan et al. | |
| 2013/0281788 A1 | 10/2013 | Garrison | |
| 2014/0031925 A1 | 1/2014 | Garrison et al. | |
| 2014/0046346 A1 | 2/2014 | Hentges et al. | |
| 2014/0135661 A1 | 5/2014 | Garrison et al. | |
| 2014/0155783 A1 | 6/2014 | Starksen et al. | |
| 2014/0257186 A1 | 9/2014 | Kerr | |
| 2014/0296769 A1 | 10/2014 | Hyde et al. | |
| 2014/0296868 A1 | 10/2014 | Garrison et al. | |
| 2014/0371653 A1 | 12/2014 | Criado et al. | |
| 2015/0025616 A1 | 1/2015 | Chang | |
| 2015/0080942 A1 | 3/2015 | Garrison et al. | |
| 2015/0150562 A1 | 6/2015 | Chang | |
| 2015/0173782 A1 | 6/2015 | Garrison et al. | |
| 2015/0174368 A1 | 6/2015 | Garrison et al. | |
| 2015/0327843 A1 | 11/2015 | Garrison | |

FOREIGN PATENT DOCUMENTS

| | | |
|---|---|---|
| JP | 2005-500138 A | 1/2005 |
| WO | WO-95/05209 A1 | 2/1995 |
| WO | WO-98/38930 A1 | 9/1998 |
| WO | WO-99/45835 A2 | 9/1999 |
| WO | WO-00/32266 A1 | 6/2000 |
| WO | WO-00/76390 A2 | 12/2000 |
| WO | WO-01/15767 A1 | 3/2001 |
| WO | WO-01/58365 A1 | 8/2001 |
| WO | WO-02/32495 A1 | 4/2002 |
| WO | WO-03/018085 A2 | 3/2003 |
| WO | WO-03/090831 A2 | 11/2003 |
| WO | WO-2004/006803 A1 | 1/2004 |
| WO | WO-2005/051206 A1 | 6/2005 |
| WO | WO-2008/144587 A2 | 11/2008 |
| WO | WO-2009/012473 A3 | 1/2009 |
| WO | WO-2009/099764 A1 | 8/2009 |
| WO | WO-2009/100210 A1 | 8/2009 |
| WO | WO-2010/075445 A1 | 7/2010 |
| WO | WO-2012/047803 A2 | 4/2012 |
| WO | WO 2015/100178 | 7/2015 |
| WO | WO 2015/175537 | 11/2015 |
| WO | WO 2016/018781 | 2/2016 |
| WO | WO 2016/036660 | 3/2016 |

OTHER PUBLICATIONS

Bergeron et al, (1999). "Percutaneous stenting of the internal carotid artery: the European CAST I Study" J. Endovasc. Surg. 6:155-159.

Bergeron et al. (2008) MEET Presentation, Cannes, French Riviera "Why I do not use routine femoral access for CAS".

Bergeron P. et al. (1996) "Recurrent Carotid Disease: Will Stents be an alternative to surgery?" J Endovasc Surg; 3: 76-79.

Bourekas, E. C., A. P. Slivka, et al. (2004). "Intraarterial thrombolytic therapy within 3 hours of the onset of stroke." Neurosurgery 54(1): 39-44; discussion 44-6.

Cohen et al., "A reappraisal of the common carotid artery as an access site in interventional procedures for acute stroke therapies", Case Reports, Journal of Clinical Neuroscience 19 (2012) pp. 323-326.

Criado et al. (1997) "Evolving indications for and early results of carotid artery stenting" Am. J. Surg.; 174:111-114.

Diederich et al. (2004) "First Clinical experiences with an endovascular clamping system for neuroprotection during carotid stenting" Eur. J. Vasc. Endovasc. Surg. 28:629-633.

Diethrich et al., (1996). "Percutaneous techniques for endoluminal carotid interventions" J. Endovasc. Surg. 3:182-202.

Diethrich, E. B. (2004). The Direct Cervical Carotid Artery Approach. Carotid Artery Stenting: Current Practice and Techniques. N. Al-Mubarak, G. S. Roubin, S. Iyer and J. Vitek. Philadephia, Lippincott Williams & Wilkins: Chapter 11. pp. 124-136.

Feldtman, R. W., C. J. Buckley, et al. (2006). "How I do it: cervical access for carotid artery stenting." Am J Surg 192(6): 779-81.

Fiorella, D., M. Kelly, et al. (2008). "Endovascular Treatment of Cerebral Aneurysms." Endovascular Today June.

Frazee, J. G. and X. Luo (1999). "Retrograde transvenous perfusion." Crit Care Clin 15(4): 777-88, vii.

Frazee, J. G., X. Luo, et al. (1998). "Retrograde transvenous neuroperfusion: a back door treatment for stroke." Stroke 29(9): 1912-6.

Goldstein "Acute Ischemic Stroke Treatment in 2007" Circ 116:1504-1514 (2007).

Gray et al. (2007) "The CAPTURE registry: Results of carotid stenting with embolic protection in the post approval setting" Cath. Cardovasc. Interven. 69:341-348.

Henry et al. (1999) "Carotid stenting with cerebral protection: First clinical experience using the PercuSurge GuardWire System" J. Endovasc. Surg. 6:321-331.

Hoffer et al. "Percutaneous Arterial Closure Devices" J. Vasc. Interv. Radiol. 14:865-885 (2003).

Howell, M., K. Doughtery, et al. (2002). "Percutaneous repair of abdominal aortic aneurysms using the AneuRx stent graft and the percutaneous vascular surgery device." Catheter Cardiovasc Intery 55(3): 281-7.

Koebbe, C. J., E. Veznedaroglu, et al. (2006). "Endovascular management of intracranial aneurysms: current experience and future advances." Neurosurgery 59(5 Suppl 3): S93-102; discussion S3-13.

Luebke, T et al. (2007) "Meta-analysis of randomized trials comparing carotid endarterectomy and endovascular treatment" Eur. J. Vasc. Endovasc. Surg. 34:470-479.

MacDonald, S. (2006) "Is there any evidence that cerebral protection is beneficial?" J. Cardiovasc. Surg. 47:127-36.

Mas et al. (2006) "Endarterectomy versus stenting in patients with symptomatic severe carotid stenosis" NEJM 355:1660-71.

MomaPresn (AET) 2002 Biamino, G; MO.MA as a distal protective device, University of Leipzig—Heart Center Department of Clinical and Interventional; Angiology Leipzig, Germany; 2002.

Nesbit, G. M., G. Luh, et al. (2004). "New and future endovascular treatment strategies for acute ischemic stroke." J Vasc Intery Radiol 15(1 Pt 2): S103-10.

Nii, K., K. Kazekawa, et al. (2006). "Direct carotid puncture for the endovascular treatment of anterior circulation aneurysms." AJNR Am J Neuroradiol 27(7): 1502-4.

Ouriel, K., R. K. Greenberg, et al. (2001). "Hemodynamic conditions at the carotid bifurcation during protective common carotid occlusion." J Vasc Surg 34(4): 577-80.

Parodi et al. (2000). "Initial evaluation of carotid angioplasty and stenting with three different cerebral protection devices" J. Vasc. Surg. 32:1127-1136.

(56) References Cited

OTHER PUBLICATIONS

Parodi, J. C., L. M. Ferreira, et al. (2005). "Cerebral protection during carotid stenting using flow reversal." J Vasc Surg 41(3): 416-22.

Perez-Arjona, E. A., Z. DelProsto, et al. (2004). "Direct percutaneous carotid artery stenting with distal protection: technical case report." Neurol Res 26(3): 338-41.

Reekers, J. A. (1998). "A balloon protection sheath to prevent peripheral embolization during aortoiliac endovascular procedures." Cardiovasc Intervent Radiol 21(5): 431-3.

Reimers et al. (2005). "Proximal endovascular flow blockage for cerebral protection during carotid artery stenting: Results froma prospective multicenter registry" J. Endovasc. Ther. 12: 156-165.

Ribo, M., C. Molina, et al. (2008). "Buying Time for Recanalization in Acute Stroke: Arterial Blood Infusion Beyond the Occluding Clot as a Neuroprotective Strategy." J Neuroimaging.

Ross, I. B. and G. D. Luzardo (2006). "Direct access to the carotid circulation by cut down for endovascular neuro-interventions." Surg Neurol 65(2): 207-11; discussion 211.

Stejskal, et al., "Experience of 500 Cases of Neurophysiological Monitoring in Carotid Endarterectomy", Acta Neurochir, 2007, 149:681-689.

Theron, et al. "New Triple Coaxial Catheter System for Carotid Angioplasty with Cerebral Protection.". AJNR 11:869-874, Sep./Oct. 1990. 0195-6108/90/1106-0869. American Society of Neurology.

\* cited by examiner

TRANSCAROTID NEUROVASCULAR CATHETER

CROSS-REFERENCE TO RELATED APPLICATIONS

This application is a Continuation of U.S. application Ser. No. 14/569,365 filed Dec. 12, 2014 entitled "Transcarotid Neurovascular Catheter", which claims priority to: (1) U.S. Provisional Application Ser. No. 62/029,799 filed Jul. 28, 2014; (2) U.S. Provisional Application Ser. No. 62/075,101 filed Nov. 4, 2014; (3) U.S. Provisional Application Ser. No. 62/046,112 filed Sep. 4, 2014; and (4) U.S. Provisional Application Ser. No. 62/075,169 filed Nov. 4, 2014; (5) U.S. Provisional Application Ser. No. 61/919,945 filed Dec. 23, 2013; and (6) U.S. Provisional Application Ser. No. 62/083,128 filed Nov. 21, 2014. The provisional patent applications are all incorporated by reference in their entirety and priority to the filing dates is claimed.

BACKGROUND

Intravascular catheters are used to access target vascular regions from remote vascular access sites to perform a procedure. The design, materials, and construction of particular catheters are primarily directed to allow the catheter to reach the target vascular anatomy while not causing vessel trauma, as well as to perform the catheter's intended function upon the catheter reaching the target anatomy. The catheter often has multiple requirements that may conflict with one another. Consequently, a strong design optimally balances the goals of these requirements.

Many catheters are single lumen catheters wherein the lumen acts as a channel for the delivery of radiopaque or therapeutic agents or for other interventional devices into the blood vessel, and/or for aspiration of blood, thrombus, or other occlusive material out of the blood vessel. Such catheters have physical properties that allow them to be advanced through a vessel access site from a proximal end into vascular anatomy which is often very curved, delicate, tortuous, and remote from the blood vessel access site. These catheters are also designed to be used with adjunctive devices such as guide wires and sometimes smaller catheters positioned in the inner lumen, and to be directed to the target anatomy through vascular access sheaths, guide catheters and sometimes sub-selective guide catheters (i.e. catheters that are specifically designed to go to more distal locations than typical guide catheters). In other words, it is often not a single catheter but a system of catheters, guide wires, guide catheters, and sheaths that allows the user to adequately perform an intended procedure.

Interventions in the cerebral vasculature often have special access challenges. Most neurointerventional procedures use a transfemoral access to the carotid or vertebral artery and thence to the target cerebral artery. However, this access route is often tortuous and may contain stenosic plaque material in the aortic arch and carotid and brachiocephalic vessel origins, presenting a risk of embolic complications during the access portion of the procedure. In addition, the cerebral vessels are usually more delicate and prone to perforation than coronary or other peripheral vasculature. In recent years, interventional devices such as wires, guide catheters, stents and balloon catheters, have all been scaled down and been made more flexible to better perform in the neurovascular anatomy. However, many neurointerventional procedures remain either more difficult or impossible because of device access challenges. In some instances, a desired access site is the carotid artery. Procedures in the intracranial and cerebral arteries are much closer to this access site than a femoral artery access site. Importantly, the risk of embolic complications while navigating the aortic arch and proximal carotid and brachiocephalic arteries are avoided. However, because most catheters used in interventional procedures are designed for a femoral access site, current devices are not ideal for the alternate carotid access sites, both in length and mechanical properties. This makes the procedure more cumbersome and in some cases more risky if using devices designed for femoral access in a carotid access procedure.

U.S. Pat. No. 5,496,294 (the '294 patent) describes a single lumen, three-layer catheter design, including (1) an inner Polytetrafluoroethylene (PTFE) liner to provide a low-friction inner surface; (2) a reinforcement layer formed of a metal coil wire or coil ribbon; and (3) an outer jacket layer. Typically, the three layers are laminated together using heat and external pressure such as with heat shrink tubing. The catheter has multiple sections of varying stiffness such that flexibility increases moving towards the distal end of the catheter. This variation in flexibility may be accomplished by varying the durometer of the outer jacket layer along the length of the catheter. Another method to vary flexibility is by varying the reinforcement structure and/or material along the length of the catheter.

One limitation in the '294 patent and in other existing neurovascular catheter technology is that the devices are designed for a femoral access approach to the cerebral arteries. The pathway from the femoral artery to the common carotid artery and thence to the internal carotid artery is both long and comprises several back and forth bends. The dimensions provided in the '294 patent are consistent with this design goal. However, catheters designed to navigate this route have lengths and flexibility transitions that would not be appropriate for a transcarotid access, and would in fact detract from performance of a transcarotid catheter. For example the flexible sections must be at least 40 cm of gradually increasing stiffness from the distal end to a proximal-most stiff section, to be able to navigate both the internal carotid artery curvature and the bends required to go from the aortic arch into the common and then the internal carotid artery.

Another disadvantage to the catheter construction described in the '294 patent is the catheter's limited ability to have continuous, smooth transitions in flexibility moving along its length. There are discreet differences in flexibility on a catheter where one jacket material abuts another, or when one reinforcement structures abuts another reinforcement structure. In addition, the tri-layer catheter construction of the '294 patent has limitations on the wall-thickness due to the need to be able to handle and assemble the three layers of the catheter during manufacture. In addition, the catheter construction makes it difficult to have a relatively large inner lumen diameter while maintaining properties of flexibility and/or kink resistance to very sharp bends in the blood vessel. As a general rule, the larger diameter catheters also tend to be stiffer in order to remain kink resistant.

SUMMARY

There is a need for a catheter with dimensions and mechanical properties which have been optimized to access the cerebral vessels from a carotid artery access site. There is also a need to for a catheter that has gradual, smooth transitions from a first flexibility to at least a second, different flexibility moving along the length of the catheter.

There is also a need for a catheter that has a relatively large inner diameter compared to prior art catheters, and yet is able to maintain physical properties such as thin wall thickness, kink resistance and flexibility.

Disclosed is an intravascular catheter that that has been optimized for accessing anterior cerebral vessels from a carotid artery access site.

Disclosed also is a catheter which includes variations in flexibility or stiffness moving along at the entire length of catheter or a portion of the length of the catheter. Advantageously, the change in flexibility of the catheter is represented by smooth, rather than sudden, changes in flexibility. In other words, the flexibility of the catheter transitions gradually moving along its length without any sudden or discrete variations in flexibility from one section of the catheter to an adjacent section of the catheter. As described in more detail below, the catheter can be particularly sized and shaped according to how the catheter will be used and in what particular section of the vascular anatomy the catheter will be used.

Also disclosed is an interventional catheter for treating an artery, comprising: an elongated body sized and shaped to be transcervically introduced into a common carotid artery at an access location in the neck, the elongated body sized and shaped to be navigated distally to an intracranial artery through the common carotid artery via the access location in the neck; an internal lumen in the elongated body, the internal lumen forming a proximal opening in a proximal region of the elongated body and a distal opening in a distal region of the elongated body; wherein the elongated body has a proximal most section and a distal most section wherein the proximal most section is a stiffest portion of the elongated body, and wherein the elongated body has an overall length and a distal most section length such that the distal most section can be positioned in an intracranial artery and at least a portion of the proximal most section is positioned in the common carotid artery during use.

Other features and advantages should be apparent from the following description of various embodiments, which illustrate, by way of example, the principles of the disclosure.

DETAILED DESCRIPTION

Figure 1A:
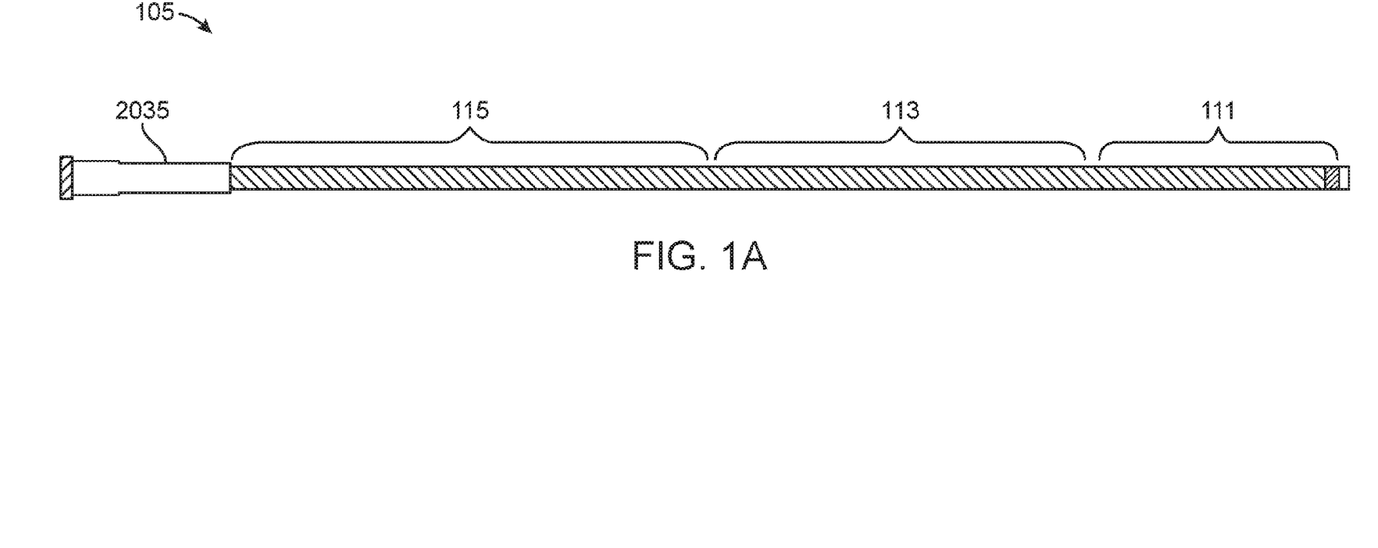
FIG. 1A shows a schematic view of an exemplary catheter.

FIG. 1A shows a schematic view of an exemplary catheter 105. The catheter 105 is an elongated body that has an external dimension that is sized and shaped for insertion into a blood vessel. In an embodiment, the catheter 105 is sized and shaped for insertion into an access sheath of a carotid artery access system such as described in U.S. patent application Ser. No. 12/834,869 entitled SYSTEMS AND METHODS FOR TREATING A CAROTID ARTERY, which is incorporated by reference herein in its entirety. U.S. patent application Ser. No. 14/537,316 entitled METHODS AND DEVICES FOR TRANSCAROTID ACCESS and filed Nov. 10, 2014 is also incorporated herein by reference in its entirety. The proximal region of the catheter 105 may have one or more mechanical or electro-mechanical control mechanisms for controlling different components on or near a distal end of the catheter 105. For example, the control mechanism(s) can be used to control inflation of a balloon or balloons, advancement/deployment of a system component (such as a stent), flushing or aspirating a fluid through the catheter, and combinations thereof With reference again to FIG. 1A, the catheter 105 is configured to be inserted through an access sheath in the carotid artery and navigated distally to the distal ICA or cerebral vessels. A proximal port 2035 with a hemostasis valve may be situated on the proximal end of catheter 105, to allow introduction of devices such as a microcatheter, guide wire, stent delivery device, aneurysm coil delivery device, or thrombectomy device while preventing or minimizing blood loss during the procedure. The hemostasis valve may be integral to the catheter proximal adaptor, or may be removably attached to the proximal end of the catheter via a proximal connector. In an embodiment, this valve is an adjustable-opening valve such as a Tuohy-Borst or rotating hemostasis valve (RHV). In another embodiment, the valve is a passive seal hemostasis valve.

The catheter 105 may be made with a two or more layer construction. In an embodiment, the catheter has a PTFE inner liner, an outer jacket layer, and at least a portion of the catheter has a reinforcement structure, such as a tubular structure formed of, for example, a wound coil, braid or cut hyptotube. In addition, the catheter may have a radiopaque marker at the distal tip to facilitate placement of the device using fluoroscopy.

The catheter 105 has an insertable portion (or working length) that is sized to be inserted through an access sheath in the carotid artery and passed through an arterial pathway (through the artery) to the distal ICA or cerebral vessels. In an embodiment adapted to be used with an access sheath of total length including the sheath hemostasis valve of about 15 to 20 cm, the catheter 105 has a working length ranging from 40 to 70 cm. The working length (or insertable portion) of the catheter is the portion of the catheter that is sized and shaped to be inserted into the artery and wherein at least a portion of the working length is actually inserted into the artery during a procedure. In an embodiment, the catheter has a working length of less than 70 cm, less than 60 cm, or less than 50 cm. A similar catheter designed for a transfemoral access site may have a working length of between 100 and 130 cm. Alternately, the length of catheter can be defined relative to the location of the access site and the target cerebral artery site. In an embodiment, the catheter is configured to be introduced into the artery at a location in the artery that is less than 40 cm, less than 30 cm, or less than 20 cm from the location of the target site as measured through the arterial pathway. The distance may further be defined by a ratio of working length to the distance between the location where the catheter enters the arteriotomy and the target site. In an embodiment, this ratio is less than 2×. In an embodiment, the working length of the device may have a hydrophilic coating to improve the ease of advancement of the device through the vasculature. In an embodiment, at least 40% of the working length of the catheter is coated with a hydrophilic material. In other embodiments, at least 50% or at least 60% of the working length of the catheter is coated with a hydrophilic material. In an embodiment, the elongated body has an overall length and a distal most section or portion length such that the distal most section can be positioned in an intracranial artery and at least a portion of the proximal most section 115 (FIG. 1A) is positioned in the common carotid artery during use while transcervically inserted into the common carotid artery.

In an embodiment, the distal-most section 111 (FIG. 1A) is constructed to be more flexible than the proximal portion, with one or more flexible sections, to successfully navigate the internal carotid artery curvature to reach target sites in the distal (internal carotid artery) ICA or cerebral arteries. The shaft may have a transition, or intermediate, section 113 of one or more increasingly stiff sections towards the more proximal section of the shaft, with the proximal most portion having the stiffest shaft section. Alternately, the transition section is a section of continuously variable stiffness from the distal section stiffness to the proximal section stiffness. In an embodiment, the distal most flexible section is between 5 and 15 cm. In another embodiment, the distal most flexible section is between 3 and 10 cm. In another embodiment, the distal section is between 2 and 7 cm. In an embodiment, the transition section is between 5 and 15 cm. In another embodiment, the transition section is between 5 and 10 cm. In another embodiment, the transition section is between 4 and 8 cm. In all these embodiments, the proximal-most stiff section takes up the remainder of the working length. In an embodiment where the catheter has a working length of 40 cm, the proximal-most stiff section is in a range 10 to 30 cm. In an embodiment where the catheter has a working length of 70 cm, the proximal-most stiff section is in a range from 40 to 60 cm. In an embodiment, the stiffest portion of the catheter is the proximal most portion of the catheter. The catheter can have a length such that, when inserted into the common carotid artery via a transcarotid entryway into the artery, the stiffest section of the catheter is located at least partially within the common carotid artery or can be positioned at least two centimeters into the common carotid artery. In an embodiment, the catheter has a length such that at least portion of the proximal most section is positioned in the common carotid artery when the distal most section is in an intracranial artery during use. The relative lengths of distal most section, transition section, and proximal most sections are not necessarily shown to scale in FIG. 1A.

Alternately, the flexible distal section and transition section may be described as a portion of the overall catheter working length. In an embodiment, the flexible distal most section is between 3 to 15% of the length of the working length of the catheter. In another embodiment, the flexible distal most section is between 4 and 25% of the length of the working length of the catheter. Similarly, in an embodiment, the transition section is between 7 and 35% of the length of the working length of the catheter. In another embodiment, the transition section is between 6 and 20% of the working length of the catheter.

In an embodiment, the flexibility of the distal most section is in the range 3 to 10 N-mm$^2$ and the flexibility of the proximal post section is in the range 100 to 500 N-mm$^2$, with the flexibility/flexibilities of the transition section falling between these two values.

As noted above, the catheter may have sections with discreet and/or continuously variable stiffness shaft. The sections of varying flexibility may be achieved by multiple methods. For example, the outer jacket layer may be composed of discreet sections of polymer with different durometers, composition, and/or thickness. In another embodiment, the outer layer has one or more sections of continuously variable outer layer material that varies in flexibility. The catheter may be equipped with the continuously variable outer layer material by dip coating the outer layer rather than laminating a jacket extrusion onto a PTFE-liner and reinforcement assembly of the catheter. The dip coating may be, for example, a polymer solution that polymerizes to create the outer jacket layer of the catheter. The smooth transition from one flexibility (e.g., durometer) to another flexibility along the length of the catheter can be accomplished via dipping the catheter assembly in multiple varying durometer materials whereby the transition from one durometer to another can be accomplished in a graded pattern, for example by dipping from one side of the catheter in one durometer with a tapering off in a transition zone, and dipping from the other side in another durometer with a tapering off in the same transition zone, so there is a gradual transition from one durometer to the other. In this embodiment, the dip coating can create a thinner walled outer jacket than a lamination assembly. In another embodiment, the catheter has an outer jacket layer that is extruded with variable durometer along the length, to provide variable flexibility along the length of the catheter.

In an embodiment, at least a portion of the catheter has a reinforcement structure, such as a tubular structure formed of, for example, a wound coil, braid that is composed of discreet or continuously varying structure to vary the stiffness, for example a variable coil or braid pitch. In an embodiment, the reinforcement structure is a cut hyptotube, with a cut pattern that is graded along the length, for example cut in a spiral pattern with continuously variable pitch or continually variable cut gap, or a repeating cut pattern that allows the tube to flex whereby the repeating pattern has a continuously variable repeat distance or repeat size or both. A cut hypotube-reinforced catheter may also have superior pushability than a coil-reinforced catheter, as it is a structure with potentially greater stability in the axial direction than a wound coil. The material for the reinforcement structure may be stainless steel, for example 304 stainless steel, nitinol, cobalt chromium alloy, or other metal alloy that provides the desired combination of strengths, flexibility, and resistance to crush. In an embodiment, the reinforcement structure comprises multiple materials along the different sections of flexibility In another embodiment the catheter has a PTFE inner liner with one or more thicknesses along variable sections of flexibility. In an embodiment, the PTFE inner liner is constructed to be extremely thin, for example between 0.0005" and 0.0010". This embodiment provides the catheter with a high level of flexibility as well as the ability to construct a thinner-walled catheter. For example, the PTFE liner is constructed by drawing a mandrel through a liquid PTFE liquid solution rather than the conventional method of thin-walled PTFE tubing manufacture, namely extrusion of a PTFE paste which is then dried and sintered to create a PTFE tube. The draw method allows a very thin and controlled wall thickness, such as in the range of 0.0005"-0.0010".

Any one of the aforementioned manufacturing methods may be used in combination to construct the desired flexibility and kink resistance requirement. Current tri-layer catheters have wall thicknesses ranging from 0.005" to 0.008". These manufacturing techniques may results in a catheter with better catheter performance at the same wall thickness, or with equal or better catheter performance at lower wall thicknesses for example between 0.003" to 0.005".

In an embodiment, the distal flexible section of the catheter may be constructed using one or more of: a dip coated outer layer, an extremely thin drawn PTFE layer, and a cut hypotube reinforcement layer, with a gradual transition from the flexible section to a stiffer proximal section. In an embodiment, the entire catheter is constructed with one or more of these elements In some instances, there is a need to reach anatomic targets with the largest possible internal lumen size for the catheter. For example the catheter may be used to aspirate an occlusion in the blood vessel. Thus there is a desire to have a very flexible, kink resistant and collapse resistant catheter with a thin wall and large inner diameter. A catheter using the construction techniques disclosed herein meets these requirements. For example, the catheter may have an inner diameter of 0.068" to 0.095" and a working length of 40-60 cm. In another embodiment, the catheter may be sized to reach the more distal cerebral arteries, with an inner diameter of 0.035" to 0.062" and a working length of 50-70 cm. In an embodiment, the catheter is configured to navigate around a 180° bend around a radius as small as 0.050" or 0.100" without kinking, wherein the bends are located within 5 cm, 10 cm, or 15 cm of the arteriotomy measured through the artery. In an embodiment, the catheter can resist collapsing whilst in a tortuous anatomy up to 180°×0.050" radius bend without collapsing when connected to a vacuum up to 20 inHg. In an embodiment, the catheter can resist collapse in the same conditions when connected to a vacuum up to 25 inHg.

Figure 1B:
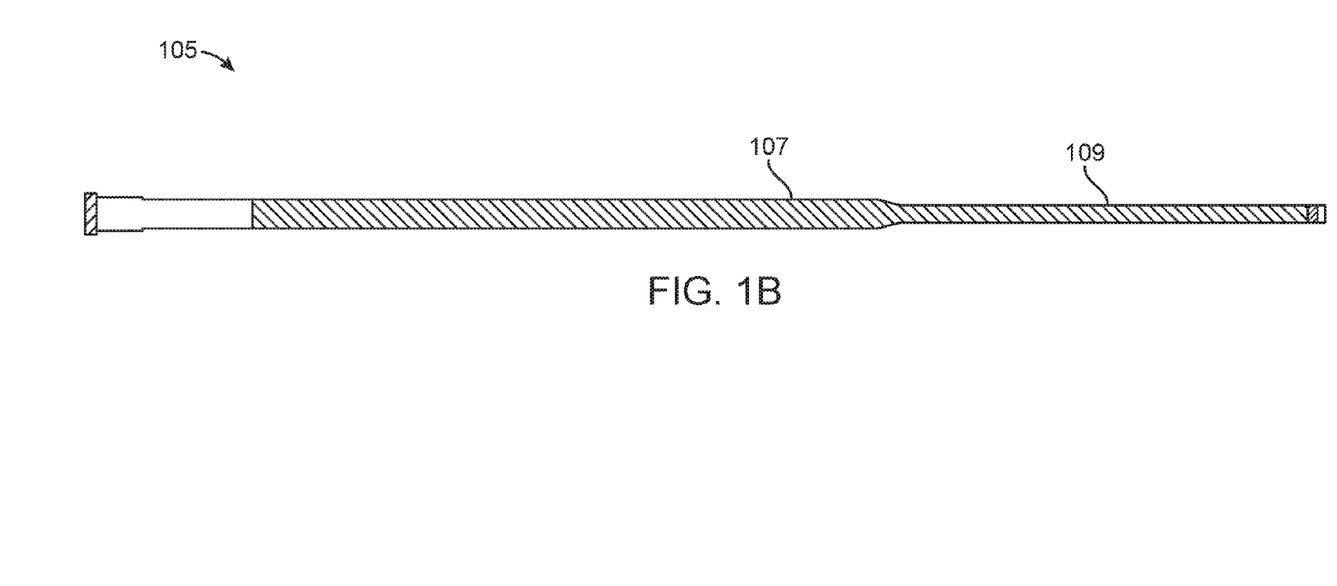
FIG. 1B shows a schematic view of an alternate embodiment of a catheter.
Figure 2:
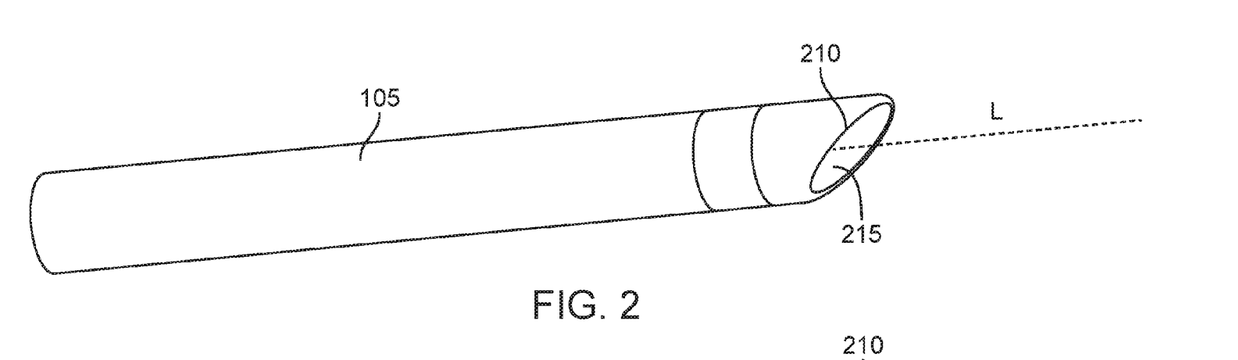
FIGS. 2-5 show examples of catheters having angled distal tips or distal edges.
Figure 3:
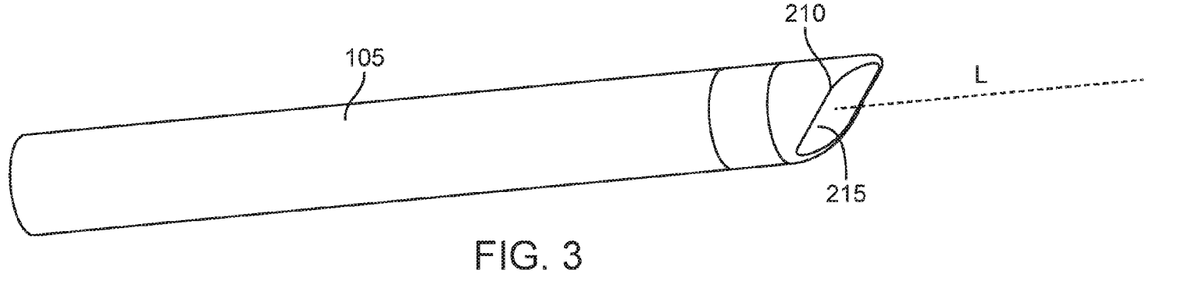
Figure 4:
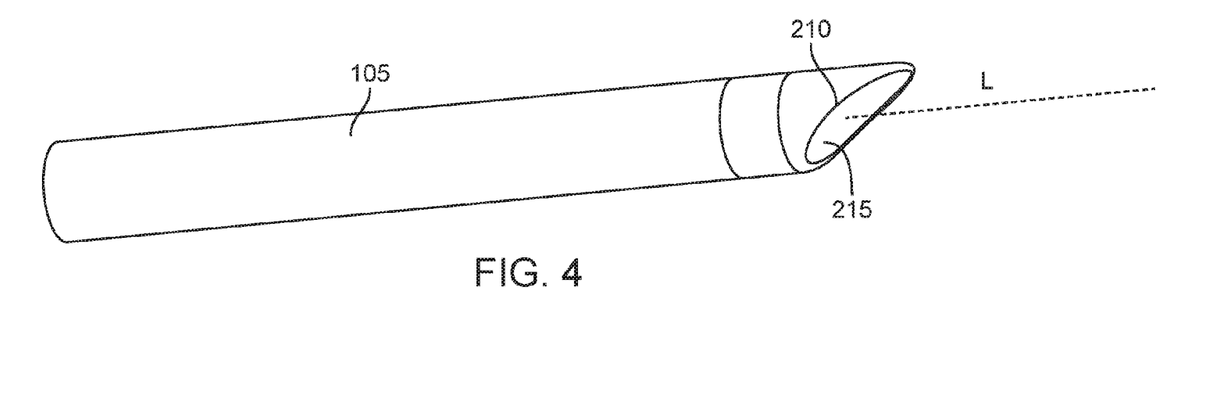
Figure 5:
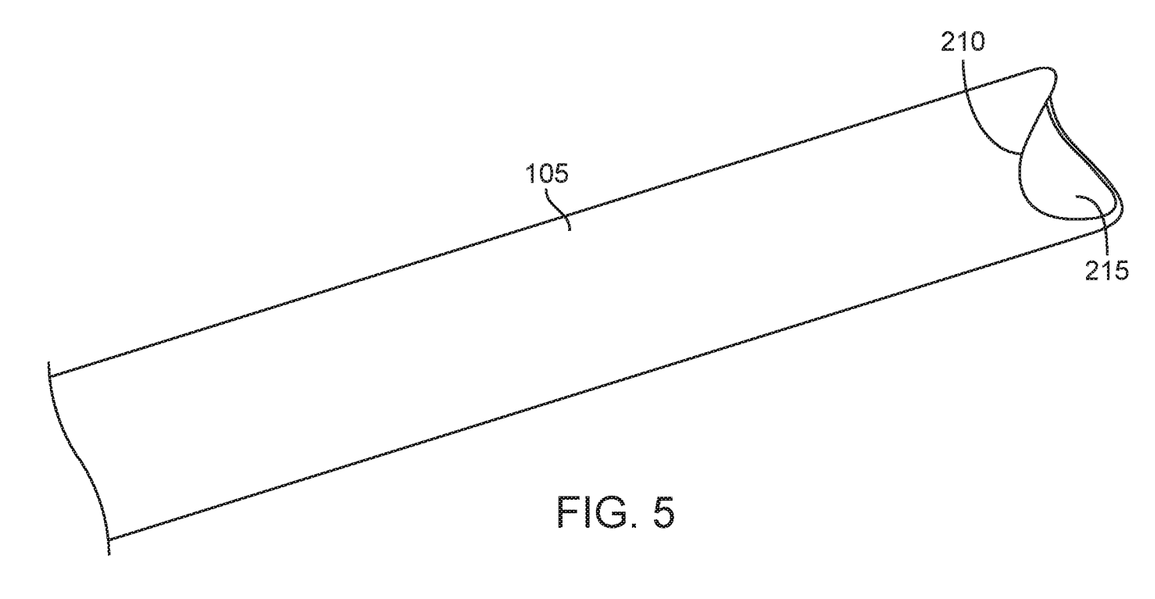

In another embodiment shown in FIG. 1B, the inner and outer diameter may be stepped up at a proximal region 107 of the catheter. The step up corresponds to an increase in diameter relative to an adjacent region of the catheter. This embodiment would further optimize the aspiration power of the catheter. For example, the portion of the catheter which is in more proximal, larger vessels during a procedure may have a larger diameter than distal region 109 of the catheter, which can be the distal most region. In this embodiment, the catheter may have a diameter for the region 109 (such as the distal most 10-15 cm), then have a step up in diameter of between 10-25% of the distal most diameter for the proximal region 107 of the working length. The step up would occur over a tapered transition section between 3 and 10 mm in length, depending on the size of the step up and the need to make a smooth transition. Alternately, the catheter is used with a stepped sheath with a larger diameter proximal region. In this case, the catheter may be stepped up a length and diameter to match the stepped sheath. For example, if the sheath has a portion with larger diameter for the proximal 20 cm of the sheath, the catheter would have a larger diameter for the proximal 25 cm to allow for additional length through proximal adaptors and valves such as an RHV. The remaining distal region would have a smaller diameter, with a step up over a tapered transition section between 3 and 10 mm in length, depending on the size of the step up and the need to make a smooth transition In some instances, a neurovascular catheter is used to aspirate clot or other obstruction in a cerebral or intracranial vessel. FIGS. 2-5 show examples of catheters having angled distal tips or distal edges. With reference to FIG. 2, the distal region of a catheter 105 is shown. The catheter 105 has a distal-most tip or edge 210 that forms an opening 215 at the distal end of the catheter 105. The distal edge 210 forms an angle that is non-perpendicular relative to the longitudinal axis L. Such a tip defines a different sized opening 215 than if the tip were perpendicular to the axis L. That is, the opening 215 is larger and presents a larger suction area relative to a distal tip that is cut normal to the longitudinal axis. The catheter therefore may provide a larger suction force on the occlusion located near the tip. The larger area opening 215 also facilitates suctioning the clot into the lumen of the catheter, rather than just capturing the clot at the tip with suction force and pulling back the captured clot with the catheter. In FIG. 2, the catheter 105 has an angled, straight edge 210 creating an elliptical opening 215. In FIGS. 3, 4 and 5, the distal edge 210 is curved or non-straight such that the distal opening 215 is non-planar and may offer greater opening without extending the tip length out as much, which may optimize the contact area with the occlusion further. The distal edge 210 may be straight, curved, undulating, or irregular. In an embodiment with a cut hypotube-reinforced catheter, the distal tip of the hypotube can be formed with the non-square shape. In an embodiment with a radiopaque marker band, the radiopaque marker band may have a non-square edge which can then be used to create the non-square catheter tip shape. In an embodiment, the catheter may have an angled distal tip. That is, the distal tip of the catheter is angled or non-perpendicular relative to a longitudinal axis of the catheter.

Figure 6:
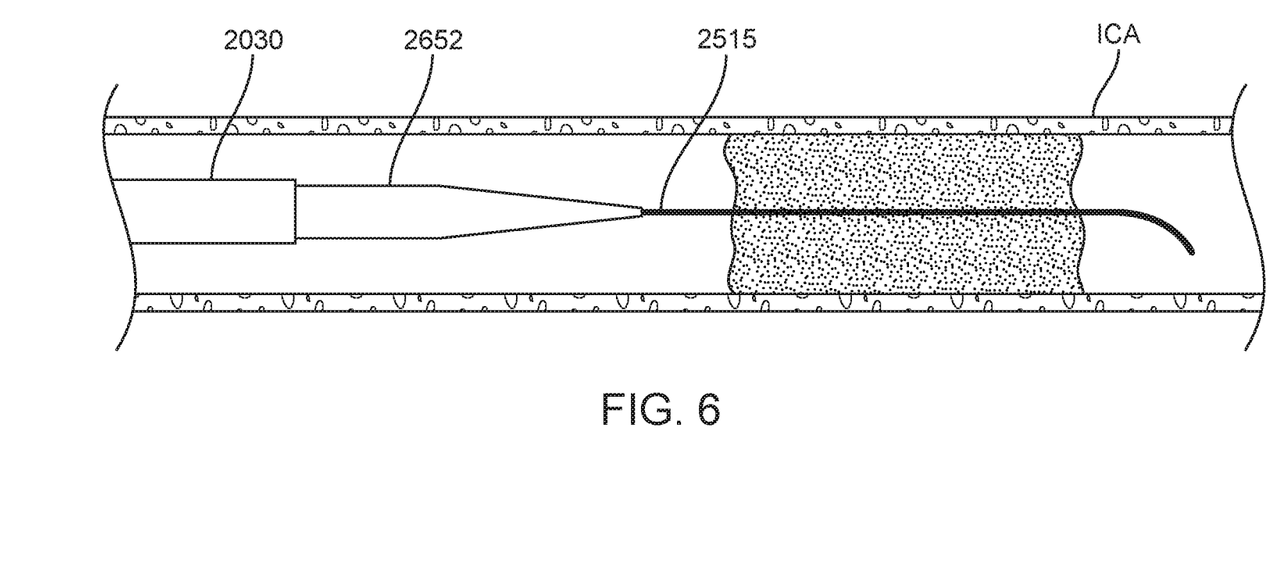
FIG. 6 illustrates an embodiment of a catheter with a tapered co-axial inner member.

A cause of difficulty in advancing catheters through severe bends and across side branches is the mismatch between the catheter and the inner guiding components such as smaller catheters, microcatheters, or guidewires. One technique for advancing a catheter is called a tri-axial technique in which a smaller catheter or microcatheter is placed between the catheter and the guide wire. However, with current systems the smaller catheter has a diameter mismatch between either the larger catheter, the guide wire, or both, which creates a step in the system's leading edge as the system is advanced in the vasculature. This step may cause difficulty when navigating very curved vessels, especially at a location where there is a side-branch, for example the ophthalmic artery. In an embodiment, as shown in FIG. 6, the catheter 105 is supplied with a tapered co-axial inner member 2652 that replaces the smaller catheter generally used. The inner member 2652 is sized and shaped to be inserted through the internal lumen of the catheter. The inner member 2652 has a tapered region with an outer diameter that forms a smooth transition between the inner diameter of the catheter 2030 and the outer diameter of a guidewire 2515 or microcatheter that extends through an internal lumen of the inner member 2652. In an embodiment, the tapered dilator or inner member 2652, when positioned within the catheter, creates a smooth transition between the distal-most tip of the larger catheter 105 and the outer diameter of a guide wire 2515 which may be in the range of 0.014" and 0.018" diameter for example. For example, the inner luminal diameter may be between 0.020" and 0.024". In another embodiment, the inner diameter is configured to accept a microcatheter with an outer diameter in the range of 0.030" to 0.040" or an 0.035" guide wire in the inner lumen, for example the inner luminal diameter may be 0.042" to 0.044".

Figure 7:
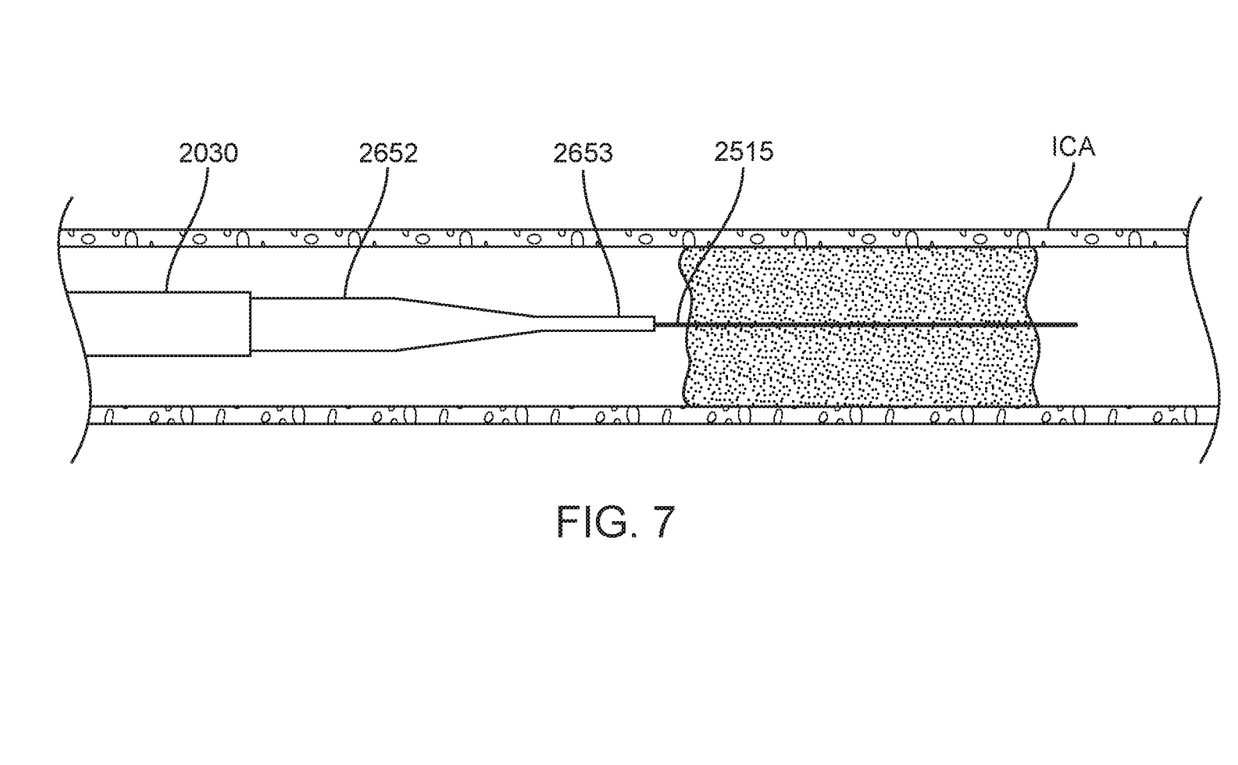
FIG. 7 illustrates another embodiment of a catheter with a tapered co-axial inner member.

In a variation of this embodiment, shown in FIG. 7, in addition to the tapered region, the inner member 2652 includes an extension formed of a uniform diameter or a single diameter, distal-most region 2653 that extends distally past the tapered portion of the inner member 2652. In this embodiment the distal region 2653 of the inner member 2652 may perform some or all of the functions that a microcatheter would do during an interventional procedure, for example cross an occlusion to perform distal angiograms, inject intraarterial agents, or deliver devices such as aneurysm coils or stent retrievers. In this manner, a microcatheter would not need to be exchanged for the dilator for these steps to occur.

The material of the dilator (inner member 2652) is flexible enough and the taper is long enough to create a smooth transition between the flexibility of the guide wire and the catheter. This configuration will facilitate advancement of the catheter through the curved anatomy and into the target cerebral vasculature. In an embodiment, the dilator is constructed to have variable stiffness, for example the distal most section is made from softer material, with increasingly harder materials towards the more proximal sections. In an embodiment, distal end of the tapered dilator has a radiopaque marker such as a platinum/iridium band, a tungsten, platinum, or tantalum-impregnated polymer, or other radiopaque marker.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. A method of treating an artery, comprising:
    introducing an interventional catheter formed of an elongated body into a common carotid artery via an access location in a neck, the elongated body sized and shaped to be introduced into the common carotid artery at the access location in the neck, wherein the elongated body includes an internal lumen forming a proximal opening in a proximal region of the elongated body and a distal opening in a distal region of the elongated body, and wherein the elongated body has a proximal most section and a distal most section wherein the proximal most section is a stiffest portion of the elongated body and wherein the elongated body has an overall length and a distal most section length such that the distal most section can be positioned in an intracranial artery and while simultaneously at least a portion of the proximal most section is positioned in the common carotid artery during use;
    (a) wherein the distal most section of the catheter has an inner diameter of 0.035 to 0.062 inch;
    (b) wherein the catheter can navigate around a 180° bend with a radius of 0.100" without kinking;
    (c) wherein the catheter does not collapse when connected to a vacuum up to 25 inHg while navigating around a 180° bend with a radius of 0.100";
    navigating the elongated body distally to an intracranial artery through the common carotid artery.

2. A method as in claim 1, wherein the elongated body includes a first transition section between the proximal section and the distal most section, and wherein the transition section has a stiffness between a stiffness of the proximal most section and the distal most section.

3. A method as in claim 1, wherein the elongated body has a working length and wherein the distal most section is between 3% and 15% of the length of the working length of the elongated body.

4. A method as in claim 1, wherein the elongated body has a working length and wherein the distal most section is between 4% and 25% of the length of the working length of the elongated body.

5. A method as in claim 2, wherein the first transition section is between 7 and 35% of the length of the working length of the catheter.

6. A method as in claim 2, wherein the first transition section is between 6 and 20% of the length of the working length of the catheter.

7. A method as in claim 3, wherein the elongated body has an inner diameter of 0.068" to 0.095" and a working length of 40-60 cm.

8. A method as in claim 3, wherein the elongated body has an inner diameter of 0.035" to 0.062" and a working length of 50-70 cm.

9. A method as in claim 1, wherein the elongated body varies in stiffness moving along at least a portion of the length of catheter.

10. A method as in claim 9, wherein the variation in stiffness is represented by smooth change in flexibility without any sudden changes in flexibility.

11. A method as in claim 9, wherein the flexibility of the elongated body transitions gradually moving along its length without any discrete variations in flexibility from one section of the elongated body to an adjacent section of the elongated body.

12. A method as in claim 1, wherein the proximal most section has a stiffness in the range of 100 to 500 N-mm2.

13. A method as in claim 1, wherein the distal most section has a stiffness in the range of 3 to 10 N-mm2.

14. A method as in claim 1, wherein the distal most section is between 5 and 15 cm in length.

15. A method as in claim 1, wherein the distal most section is between 3 and 10 cm in length.

16. A method as in claim 2, wherein the first transition section is between 5 and 10 cm in length.

17. A method as in claim 2, wherein the first transition section is between 4 and 8 cm in length.

18. A method as in claim 1, wherein the elongated body has a working length of 40 cm and the proximal most section has a length of 10 to 30 cm.

19. A method as in claim 1, further comprising inserting an inner member inside the internal lumen of the elongated body, the inner member having a tapered leading edge.

* * * * *